United States Patent
Schmitt et al.

(10) Patent No.: US 6,488,705 B2
(45) Date of Patent: *Dec. 3, 2002

(54) RADIALLY SELF-EXPANDING IMPLANTABLE INTRALUMINAL DEVICE

(75) Inventors: Peter J. Schmitt, Garnerville, NY (US); David J. Lentz, Randolph, NJ (US)

(73) Assignee: Meadox Medicals, Inc., Oakland, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/955,266

(22) Filed: Sep. 18, 2001

(65) Prior Publication Data

US 2002/0026237 A1 Feb. 28, 2002

Related U.S. Application Data

(60) Continuation of application No. 09/056,081, filed on Apr. 7, 1998, now Pat. No. 6,299,636, which is a division of application No. 08/461,040, filed on Jun. 5, 1995, now Pat. No. 5,824,034, which is a division of application No. 07/945,064, filed on Sep. 14, 1992, now Pat. No. 5,562,725.

(51) Int. Cl.$^7$ .................................................. A61F 2/06
(52) U.S. Cl. ........................................................ 623/1.18
(58) Field of Search ................................ 623/1.1, 1.11, 623/1.12, 1.13, 1.14, 1.15, 1.16, 1.17, 1.18, 1.19, 1.2, 1.21, 1.22, 1.25, 1.3, 1.32, 1.33, 1.36, 1.49, 1.5, 1.51, 1.53; 606/108, 191, 194, 195; 600/198

(56) References Cited

U.S. PATENT DOCUMENTS

| | | |
|---|---|---|
| 2,978,787 A | 4/1961 | Liebig |
| 3,095,017 A | 6/1963 | Bleiler et al. |
| 3,105,492 A | 10/1963 | Jeckel |
| 3,253,618 A | 5/1966 | Cook |
| 3,272,204 A | 9/1966 | Artandi et al. |

(List continued on next page.)

FOREIGN PATENT DOCUMENTS

| | | |
|---|---|---|
| EP | 0 177 072 A1 | 8/1984 |
| EP | 0 183 372 A1 | 6/1986 |
| EP | 0 493 788 A1 | 7/1992 |
| FR | 2548225 A1 | 1/1985 |
| GB | 2189150 A | 10/1997 |
| WO | WO 83/03752 | 11/1983 |
| WO | WO 88/00813 | 2/1988 |
| WO | WO 88/06026 | 8/1988 |
| WO | WO 90/15582 | 12/1990 |
| WO | WO 91/10766 | 7/1991 |
| WO | WO 92/16166 | 10/1992 |

OTHER PUBLICATIONS

R.T. Brown, "Three–Dimensional Braiding", *Handbook of Industrial Braiding*.

Zollikoifer, C., et al., "Historical Overview on the Development of characteristics of Stents and Outlooks", Cardiovascular and Interventional Radiology, 15, 272–278 (1992).

Primary Examiner—Michael J. Milano
Assistant Examiner—Vy Q. Bui
(74) Attorney, Agent, or Firm—Hoffman & Baron, LLP

(57) ABSTRACT

A radially self-expanding implantable intraluminal device formed from a hollow tubular braid. The intraluminal device may be used in a variety of medical procedures which require a passageway to be maintained in an open position or which require reinforcement, support or a bypass conduit such as in blood vessels weakened by disease. The intraluminal device is longitudinally expanded or radially collapsed for ease of insertion into a lumen and upon alignment within the lumen, the intraluminal device radially self-expands to come into intimate contact with the inner surface of the lumen.

15 Claims, 3 Drawing Sheets

U.S. PATENT DOCUMENTS

| | | | |
|---|---|---|---|
| 3,316,557 A | 5/1967 | Liebig | |
| 3,317,924 A | 5/1967 | Le Veen | |
| 4,193,137 A | 3/1980 | Heck | |
| 4,587,075 A | 5/1986 | Butcher et al. | |
| 4,655,771 A | 4/1987 | Wallsten | |
| 4,719,837 A | 1/1988 | McConnell et al. | |
| 4,740,207 A | 4/1988 | Kreamer | |
| 4,743,250 A | 5/1988 | Kitagawa et al. | |
| 4,776,337 A | 10/1988 | Palmaz | |
| 4,820,298 A | 4/1989 | Leveen et al. | |
| 4,913,141 A | 4/1990 | Hillstead | |
| 4,917,699 A | 4/1990 | Chervitz | |
| 5,007,926 A | 4/1991 | Derbyshire | |
| 5,026,377 A * | 6/1991 | Burton et al. | 606/108 |
| 5,078,726 A | 1/1992 | Kreamer | |
| 5,084,065 A | 1/1992 | Weldon et al. | |
| 5,108,416 A | 4/1992 | Ryan et al. | |
| 5,151,105 A | 9/1992 | Kwan-Gett | |
| 5,242,451 A | 9/1993 | Harada et al. | |
| 5,360,443 A | 11/1994 | Barone et al. | |
| 5,383,925 A | 1/1995 | Schmitt | |
| 5,395,390 A | 3/1995 | Simon et al. | |
| 5,406,055 A | 4/1995 | McGaffigan | |
| 5,536,274 A | 7/1996 | Neuss | |
| 5,545,208 A * | 8/1996 | Wolf et al. | 623/1 |
| 5,653,759 A | 8/1997 | Hogan et al. | |
| 5,676,697 A | 10/1997 | McDonald | |
| 5,718,159 A * | 2/1998 | Thompson | 87/33 |
| 5,723,003 A | 3/1998 | Winston et al. | |
| 5,741,325 A * | 4/1998 | Chaikof et al. | 623/1 |

* cited by examiner

RADIALLY SELF-EXPANDING IMPLANTABLE INTRALUMINAL DEVICE

The present application claims priority to and is a continuation application of application U.S. Ser. No. 09/056,081 (now U.S. Pat. No. 6,299,636), filed Apr. 7, 1998, which is a division of U.S. Ser. No. 08/461,040 (now U.S. Pat. No. 5,824,034) filed Jun. 5, 1995, which is a division of U.S. Ser. No. 07/945,064 (now U.S. Pat. No. 5,562,725) filed Sep. 14, 1992.

BACKGROUND OF THE INVENTION

The present invention relates to an implantable intraluminal device. More specifically, the present invention relates to a radially self-expanding implantable intraluminal device which is particularly useful for repairing or serving as a conduit for blood vessels narrowed or occluded by disease or for use in other body passageways requiring reinforcement or the like.

Intraluminal devices or, more specifically, endovascular prosthesis, are known for treating stenosis, stricture, aneurysm conditions and the like. These devices, which include stents and grafts, are generally implanted by a mechanical transluminal procedure. Stents are devices designed to hold open a constricting vessel and generally are not designed as conduits or bypass devices. Intraluminal or endoprosthetic graphs, on the other hand, are designed as internal bypass devices which relieve stress from the surrounding vessel wall. Often, a device of this type is percutaneously implanted within the vascular system to reinforce collapsing, partially occluded, weakened or abnormally dilated localized sections of a blood vessel. Advantages of this method over conventional vascular surgery include obviating the need for surgically exposing, incising, removing, replacing, or bypassing the defective blood vessel. Stents are often used in combination with other endoprosthesis, such as intraluminal grafts. In some cases a stent is positioned at each end of the graft, thus allowing the graft to serve as a conduit or internal support to relieve stress from the vessel wall. The stents on each end serve to keep the lumen open and to anchor the graft in place. Attachment of the graft to the stent can be accomplished with hooks or sutures. In some instances, the stent is attached to only one end of the intraluminal graft. In this case the graft is allowed to "float" in the downstream direction of the vessel.

Structures which have previously been used as stents have included coiled stainless steel springs; helically-wound coiled springs manufactured from an expandable heat-sensitive material; expanding stainless steel stents formed of stainless steel wire in a zig-zag pattern; cage-like devices made from malleable metal; and flexible tubes having a plurality of separate expandable ring-like scaffold members which permit radial expansion of the tube. Each of these devices is designed to be radially compressible and expandable so that they will easily pass through a blood vessel in a collapsed state and can radially expand to an implanted size after the problem area has been reached. None of these devices is designed to retain fluid.

Each of the foregoing structures suffer from a number of disadvantages. To begin with, current stents are not designed to be contractible once deployed and therefore a great deal of care must be taken to properly position and expand the device to the appropriate size. Over expansion of a stent places unnecessary stress on an already damaged vessel. Under expansion of the stent may result in inadequate contact with the inner wall of the vessel and migration of the stent may occur.

Because the structures are designed to be delivered in a collapsed state within a blood vessel, it is difficult to ensure that the device, once deployed, will radially expand to the proper dimensions. For example, the expansion of a particular coiled spring-type stent is predetermined by the spring constant and modulus of elasticity of the particular material used to manufacture the coiled spring structure. These same factors predetermine the amount of expansion of collapsed stents formed of stainless steel wire in a zig-zag pattern. Likewise, prostheses formed from heat sensitive material which expands upon heating have a predetermined amount of expansion based upon the alloy utilized in their manufacture.

Another type of endovascular prosthesis consists of a thin wall textile radially fixed graft, which is folded up to fit inside an introducer sheath. The graft is manufactured to a predetermined diameter. If the graft is oversized, when displaced in the artery and subsequently expanded, the graft may not fully open leaving a fold or a crease in the graft which may further constrict an already narrowed or occluded blood vessel. On the other hands if the graft is too small in diameter, it will slide around in the vessel and disrupt blood flow.

As previously mentioned, intraluminal grafts are often used in combination with stents. Another disadvantage of the foregoing types of intraluminal devices is that once the device is deployed within the lumen, it is permanently and fully expanded and cannot be contracted for repositioning. It is advantageous to be able to realign an intraluminal graft which has been misdeployed through catheter malfunction or any other problem which may arise during the implantation procedure. Generally, the present intraluminal devices once fully expanded cannot be easily moved within the lumen without surgery.

When repairing blood vessels narrowed or occluded by disease, or repairing other body passageways, the device used in repairing or supporting the passageway must be flexible enough to negotiate the curves or bends of the body passageway. Most conventional endovascular prostheses do not have the requisite ability to bend so as to be advantageously placed within the vascular system.

Accordingly, it would be desirable to develop a new and improved intraluminal device and, in particular, an intraluminal vascular graft that can be expanded to a variable size to accommodate the size of the diseased portion of the vessel and prevent migration of the graft away from the desired location and provide support functions similar to conventional stents. The intraluminal grafts of the present invention are directed toward achieving this result as well as others including: preventing rupturing and/or erosion of the body passageway by the expanded graft; permitting tissue of an elongated section of a body passageway to be supported by an elongated graft; providing the necessary flexibility to negotiate the bends and curves of a vascular system; and being repositionable and adjustable even after being radially expanded within the lumen. Therefore, an intraluminal vascular graft which would overcome the foregoing difficulties and others while providing better and more advantageous overall results is highly desirable.

SUMMARY OF THE INVENTION

In accordance with the present invention, a new and improved radially self-expanding implantable intraluminal device is provided. More particularly, the present invention is formed from a hollow tubular braid which may be implanted intraluminally and thereafter radially self-expands to come in intimate contact with the inner surface of the lumen in which it is inserted.

The device is preferably used as an endovascular prosthesis in which the device relieves the stress of weakened blood vessel, although it may be used in a variety of body passageways to provide reinforcement of a supporting passageway or the like. The implantable intraluminal device is both radially and longitudinally flexible or bendable. When the tubular braid is elongated in the longitudinal direction, the diameter of the device is decreased so that it may be percutaneously implanted within a body passageway. Once the device has been properly positioned within the body passageway, it is permitted to radially self-expand or self-deploy to come in intimate contact with the interior surface of the body passageway.

The hollow tubular braid may be formed from a number of natural and synthetic materials, including collagen, thermoplastics and metals. More specifically, thermoplastics which are useful include polyesters, polypropylenes, polyethylenes, polyurethanes, or polytetrafluoroethylenes and combinations and mixtures thereof. Useful metallic substances include stainless steel, titanium and nichol-chromium alloys, among others. The hollow tubular braid is formed to be radially self-expanding by heat-conditioning the thermoplastic or metal fibers from which the device is made at a sufficient time and temperature to effectuate memory. The braid is heat-conditioned in a radially expanded or longitudinally compressed position to provide the radially self-expanding feature of the device. For example, if the thermoplastic chosen for making a tubular braid is polyester, the tubular braid is preferably heat conditioned at a temperature from about 200° F. to about 700° F. for approximately five to thirty minutes and subsequently cooled while being maintained in a radially expanded position, thereby effectuating memory within the braided device.

The type of braid used to form the tubular device may be varied. More specifically, the intraluminal device of the present invention may be formed from a simple three yarn tubular braid (two-dimensional braid) or may be formed from a three-dimensional braid. The braid may also include a yarn which is used to stiffen the tubular braided structure and provide a greater radially expanding force. The expanding radial force is preferably designed so that the intraluminal device will open up to be in intimate contact with the interior surface of the body passageway in which it is inserted and anchor itself thereto.

Generally, the fibers used to form the braid have a denier in the range of 20 to 500 denier, although deniers outside this range may have utility for specific applications. The force exerted by the device is non-rupturing, i.e., sufficient to open the device without causing damage to the vessel wall. The braid may be formed with a braid angle between 15° and about 90° and preferably about 54.50 to about 75° with respect to the longitudinal axis of the braided structure. The braid angle is measured from the longitudinal axis of the braided device.

Once inserted into the body passageway, the intraluminal device will be permitted to radially self-expand and substantially conform to the shape and inner surface of the body passageway. The intraluminal device need not be perfectly sized to the vessel or passageway into which the device is inserted since the diameter of the device is infinitely variable in the ranges between its minimum diameter and its maximum diameter.

An advantage of the radially self-expanding implantable intraluminal device of the present invention is that once it is inserted and permitted to self-expand, the device may still be repositioned or realigned if not properly positioned within the lumen. A method of repositioning an implanted intraluminal device of the present invention includes introducing a guide wire having on its distal end a means or mechanism, such as a finger-like member, for grasping the braided device so that the device may be realigned to a proper position within the lumen. By pulling on one end of the intraluminal device of the present invention, the device will elongate in the longitudinal direction causing a decrease in diameter of the device such that it is free to move within the vessel, thereby permitting the device to be easily repositioned. Once in the repositioned location and no longer longitudinally elongated, the device of the present invention will once again radially self-expand to come into intimate contact with the inner surface of the lumen.

One method of producing a radially self-expanding implantable intraluminal device includes radially expanding a hollow tubular braid and subjecting the radially expanded braid to conditions of time and temperature sufficient to set the material in the radially expanded position. As a consequence of radial expansion, the device is shortened in length due to changes in the angle of the yarns with respect to the longitudinal axis. The braid is then permitted to cool while maintaining the braid in the radially expanded position. The heat source for heat conditioning the thermoplastic braid includes a convection oven, a heated mandrel, an infra-red light source or immersing the device in a hot liquid medium. The thermoplastic braid is preferably heated at a temperature of about 200° F. to about 700° F. for a time period of about five to thirty minutes. However, the heat parameters will vary depending upon the thermoplastic selected for forming the tubular braid. The heat conditioning of the thermoplastic yarns of the braid provides the intraluminal device of the present invention with memory to return the device to a radially expanded position following a reduction in diameter due to longitudinal expansion so that the device may be intraluminally inserted into a body passageway.

In an alternative embodiment of the present invention, the intraluminal device may also include a means for attaching the device to the inner surface of the lumen to provide additional anchoring of the device. Such attaching means may include small hooks which are integrally formed on the outside or extraluminal surface of the device during the braiding process. Preferably, the hooks are integrally formed in at least one end of the device, although, depending upon the procedure being performed, both ends may include hooks. Anchoring means may also be added as a separate component if desired.

A preferred form of the intraluminal device, as well as other embodiments, features and advantages of this. invention will be apparent from the following detailed description of illustrative embodiments thereof, which is to be read in connection with the accompanying drawings.

DETAILED DESCRIPTION OF THE INVENTION

Figure 1:
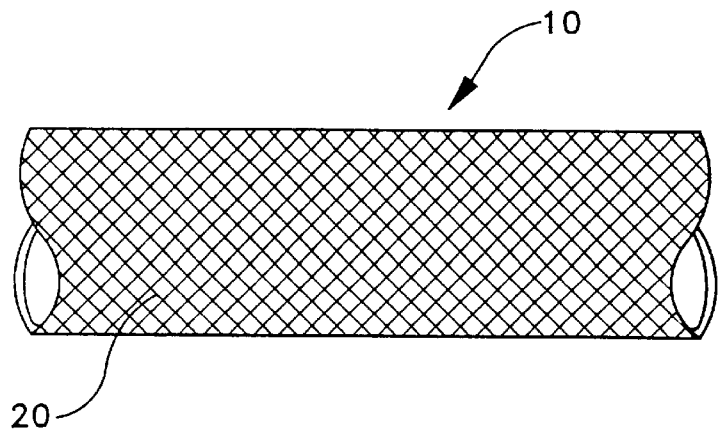
FIG. 1 is a side elevational view of the intraluminal device of the present invention shown in a radially expanded position.
Figure 2:
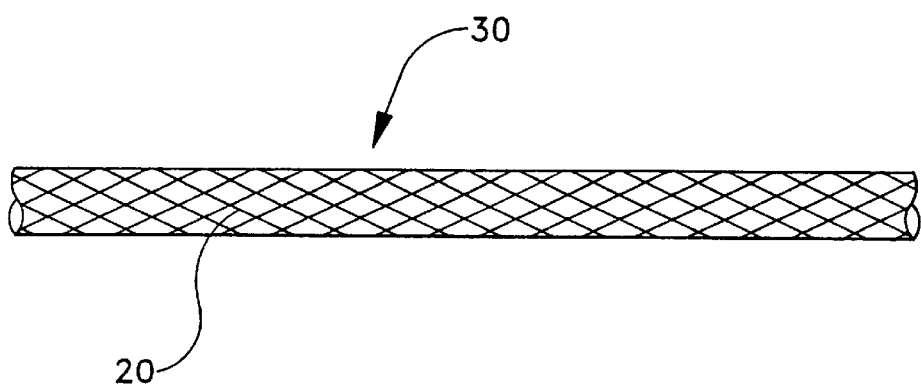
FIG. 2 is a side elevational view of the intraluminal device of the present invention shown in a longitudinally expanded, radially collapsed insertion position.

FIGS. 1 and 2 illustrate a radially self-expanding implantable intraluminal device formed from a hollow tubular thermoplastic braid. For purposes of describing the present invention, the terms "intraluminal device" and "radially self-expanding prosthesis" are interchangeably used in describing the methods, apparatus and structures of the present invention. The intraluminal device may be used not only as an intraluminal vascular graft for supporting a diseased or damaged vessel, but its radially self-expanding capabilities give it a stent-like feature for expanding partially occluded segments of a blood vessel or body passageway. Many other procedures which require a radially expandable prosthesis for a variety of body passageways are contemplated.

The intraluminal device of the present invention may especially be used in the following procedures: supportive graft placement within blocked blood vessels opened by transluminal recanalization, but which are likely to collapse in the absence of an internal support; a supporting graft structure following passage of a catheter through vessels occluded by inoperable cancers; supportive graft placement of narrowing of the esophagus, the intestine and the urethra; and supportive graft reinforcement of reopened and previously obstructed bile ducts. Accordingly, the terms "prosthesis" and "intraluminal device" encompass the foregoing usages within various body passageways or lumens. Further in this regard, the term "body passageway" encompasses any duct within the human body, such as those previously described, as well as any vein, artery or blood vessel within the human vascular system.

Figure 5A:
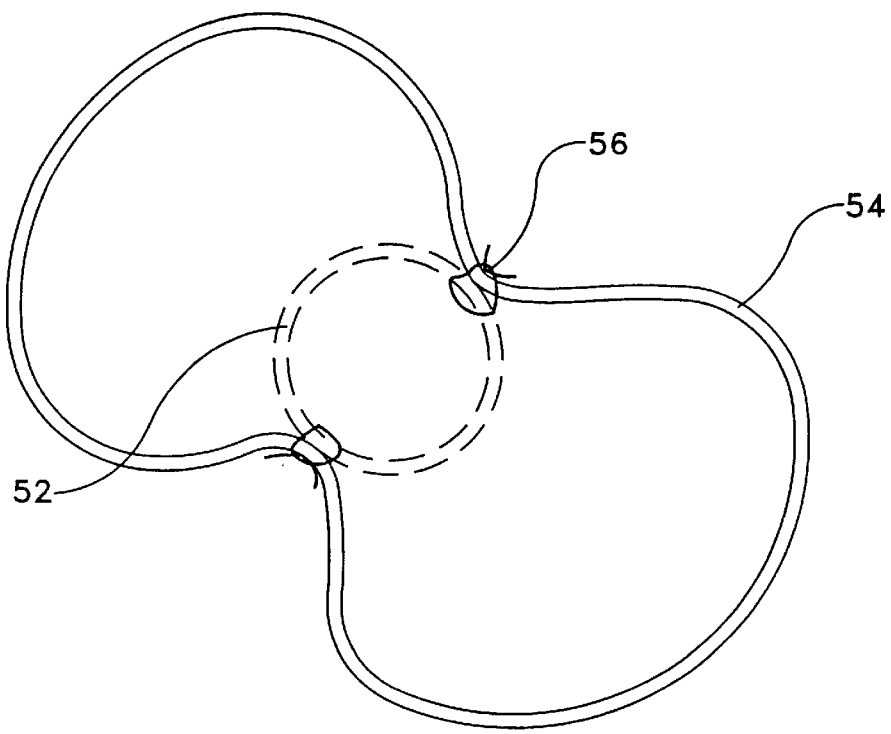
FIG. 5a is a cross-sectional view of a prior art stent-graft combination in an unexpanded state.
Figure 5B:
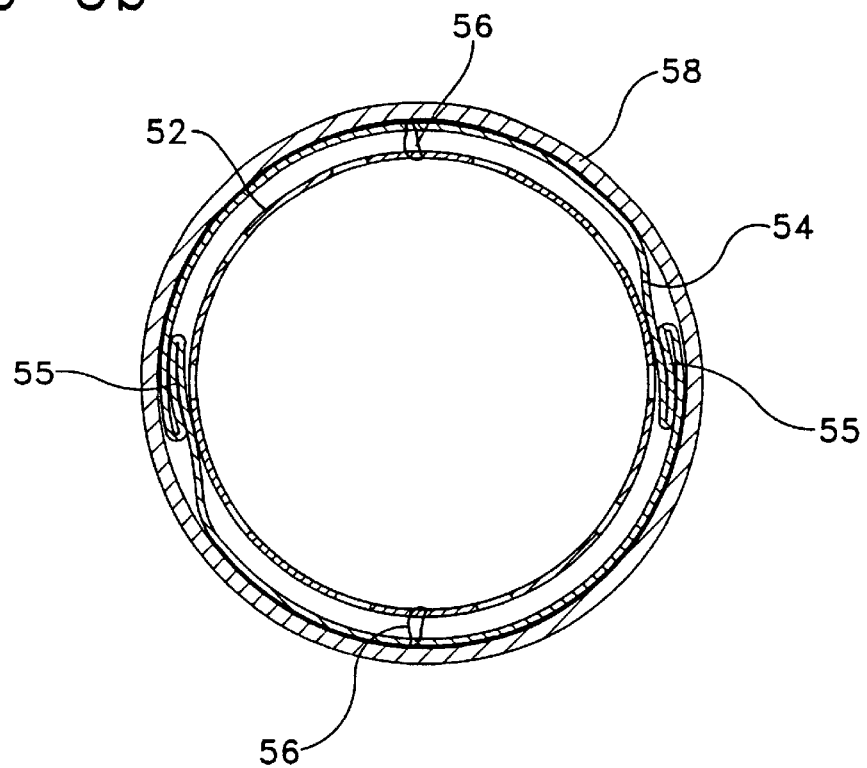
FIG. 5b is a cross-sectional view of a prior art stent-graft combination in an expanded state within a lumen.

FIGS. 5a and 5b illustrate a prior art graft-stent combination used to open constricted lumens as well provide a support for a weakened lumen. Referring to FIG. 5a, an unexpanded stent 52 is illustrated positioned within a graft 54. The graft 54 is attached to the stent 52 by means of sutures 56. As illustrated in FIG. 5b, this stent-graft combination may be inserted into a body lumen and once correctly positioned, the stent 52 is radially expanded to bring the stent-graft combination into contact with the inner wall of the lumen 58. The graft 54 is pressed against the inner wall of the lumen 58 by the expansion of the stent 52. The diameter of the graft shown in FIG. 5b was oversized and upon expansion by the stent, folds or creases 55 were formed in the graft because the graft could not be fully expanded. The folds 55 may further weaken an already weakened lumen by placing excessive force on the lumen in the areas of contact. Accordingly, it would be advantageous to be able to properly size the stent-graft combination to form a more exact fit within the lumen.

FIG. 1 illustrates a preferred embodiment of the present invention in its radially expanded position. The intraluminal device of the present invention is in the form of a hollow tubular braid. The tubular braid may be any type of braid, for example either a simple, conventional braid, i.e., a two-dimensional braid, or a three-dimensional braid. A braided structure is ideally suited for making tubular structures which can radially expand and contract, thereby forming a structure with an infinitely variable diameter within certain minimum and maximum values.

The tubular braid is preferably a simple, conventional two-dimensional braid formed from two sets of yarns spiralling in opposing directions about a longitudinal axis of the tube being formed. The braid angle (helix angle) of the tubular braid is the angle in relation to the longitudinal axis of the tube being formed and may vary from about 15° to 70°. The tubular braid is formed so that the yarn components 20 can scissor through severe angle changes thereby altering the diameter of the tubular structure. In this regard, a tubular braid can be formed which can be radially collapsed or longitudinally extended or elongated to form a small diameter for implanting intraluminally into a body passageway. Following insertion and positioning within the lumen, the device of the present invention will radially self-expand or longitudinally compress to form a relatively large diameter tube by causing the yarns 20 to scissor to the larger diameter. This type of braided structure maintains structural integrity even when undergoing these geometric changes because the two opposing yarn systems are interwoven. The yarns 20 are sufficiently spaced to allow them to move freely in place. As can be seen comparing a radially collapsed tubular braid shown in FIG. 2 with a radially expanded tubular braid shown in FIG. 1, the space between the yarns will decrease as the diameter increases.

For example, FIG. 1 illustrates a tubular braid of the present invention in its radially expanded state 10 and FIG. 2 illustrates the same tubular braid in its radially collapsed state 30. In the radially collapsed state, the tubular braid may have a diameter of 6 millimeters whereas in the radially expanded state the diameter may be 18 millimeters. In this example, the diameter increase is three fold, and therefore, the ratio of the sine of the helix angle for the radially expanded tubular braid should be three times that for the radially collapsed tubular braid. If the helix angle is 15° when the diameter of the tube is 6 millimeters, then the helix angle when the diameter is increased will be about 51°. This is mathematically proven by taking the sine of 15° which is 0.2588, multiplying this value by three to yield 0.7764 and taking the inverse sine to arrive at a helix angle of about 51° and a diameter of 18 mm.

Another characteristic of the tubular braided structure of the present invention which makes it highly desirable for use as an endovascular prosthesis is the flexibility of the structure. In a diseased or occluded blood vessel, the blood flow may be distorted or disturbed due to irregularities on the inner surface of the blood vessel as well as the bends or curves of the vessel. The tubular braided structure of the present invention is highly flexible and bendable both in the radial and longitudinal directions, can negotiate any curves or bends formed in the blood vessel and can conform to inner surface conditions found within the blood vessel. The tubular braid can be bent to angles approaching 180° and still maintain an open lumen through the bend. The yarns 20 used to produce the flexible tubular braid preferably have a denier in the range of 20 to 500 denier whereby the smaller the yarn denier, the finer or thinner the yarn.

The selection of the yarn denier, type of yarn and braid angle and the number of carriers will also determine the porosity of the structure. These factors also dictate the strength and diameter of the device. The intraluminal device of the present invention is most likely to be used to support a weakened body passageway or maintain an opening in an occluded body passageway. Accordingly, the porosity of the device should be sufficient to allow ingrowth of surrounding tissue into the structure to encourage assimilation and anchorage of the device within the body passageway.

The yarns 20 used to form the tubular braid are preferably thermoplastics and metallic material. Suitable thermoplastic materials for forming the braid of the intraluminal device of the present invention include but are not limited to polyester, polypropylene, polyethylene, polyurethane and polytetraflouroethylene. Suitable metallic materials for forming the braid of the intraluminal device of the present invention include but are not limited to stainless steel, titanium and a nickel-chromium alloys, among others. A thermoplastic yarn is preferably used so that, upon heat conditioning in the radially expanded state the braid becomes heat set with elastomeric memory and a natural tendency to return to this position. Thus, the braided device is radially self-expanding when restraining forces are removed. The braid may be formed on a mandrel having the diameter equal to the maximum expanded diameter of the braid. Alternatively, the tubular braid can be braided at a smaller diameter and heat set at a larger diameter. Thus, when the intraluminal device is in an unstressed condition, the tubular braid will be in the radially expanded state. The heat conditioning of the thermoplastic braid effectuates memory. More specifically, the tubular braid contracts in diameter when placed under longitudinal stress, or in other words, radially compresses. When the longitudinal stress is removed, the tubular braid radially self-expands or returns to its original position or diameter, i.e., approximately the diameter at which the device was heat conditioned or the diameter of the vessel in which it is contained. The tubular braid of the present invention may also include a stiffening component, such as polymeric or metallic wires, to add a greater degree of stiffness, rigidity and resiliency to the structure. The stiffening component could also provide the intraluminal device of the present invention with a greater self-expanding or spring-like force. Additionally, the tubular braid of the present invention may include axial yarns which are braided into the structure to limit or control the amount of expansion of the device when in an unstressed state.

The method for making the intraluminal device of the preferred embodiment includes forming a tubular braid from a yarn and preferably a thermoplastic yarn. The tubular braid is preferably formed having a small diameter and is thereafter placed in a radially expanded state for heat conditioning. A preferred method for heat conditioning includes placing the tubular braid on a mandrel so that the braid is radially expanded. The radially expanded thermoplastic braid is then heat-conditioned or heat set at a sufficient time and temperature to effectuate memory. The heating time and temperature is dependent upon the yarn material chosen to form the braid. Upon completion of the heating process, the tubular braid is cooled while maintaining the braid in the radially expanded position.

For example, if the thermoplastic chosen is polyester, the radially expanded tubular braid is preferably heat conditioned at a temperature between 300° F. and 400° F. for approximately ten to thirty minutes. The heating process may be accomplished by a variety of heating methods. The heating methods include but are not limited to the use of a convection oven, an infra-red light source, immersing the tubular braid in a hot liquid medium or by heating the mandrel on which the tubular braid is radially expanded. Following heat conditioning, the tube is maintained in the radially expanded position and cooled to ambient temperature. An additional step in the process optionally includes a cleaning or scouring process of the tubular braid prior to or following heat conditioning in order to remove any residuals which may be present on the tube from the braiding process. The cleaning is preferably performed using water or compatible solvents and cleaning agents.

The advantage of using the thermoplastic yarn and heat treating the tubular braid is that the intraluminal device formed by this process is radially self-expanding. Thus, the intraluminal device of the present invention does not require expansion in-vivo by a balloon catheter, such as the majority of mechanical stents available for use as an endovascular prosthesis. The intraluminal braided device of the present invention is radially self-expanding and has the stent feature inherently incorporated into the device.

Figure 6:
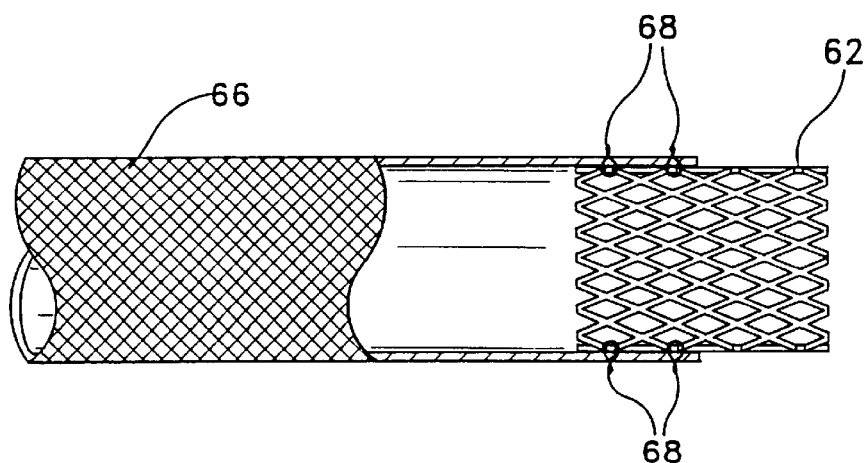
FIG. 6 is a side elevational view of a stent-graft combination of the present invention.

The present devices can be effectively used in combination with other prosthetic devices such as stents as illustrated in FIG. 6. This alternative embodiment of a stent-graft combination includes at least one stent 62, coupled to an intraluminal device 66 formed in accordance with the present invention. The stent 62 is secured to the end of the intraluminal device 66 by means of hooks or sutures 68. The stent 62 serves to keep the lumen open and to enhance anchoring the intraluminal device 66 in position. The intraluminal device 66 formed in accordance with the present invention is radially self-expanding and, therefore radially expands along with the expansion of the stent. The intraluminal device 55 may be used to support a weakened or diseased vessel.

As previously mentioned, tubular endoprothesis devices, i.e., intraluminal grafts, have been used in combination with stents which were not self-expanding or radially adjustable. Also these tubular endoprosthetic devices were fixed in diameter and were therefore not capable of being radially adjustable. Thus, this conventional combination use of stent and tubular endoprosthetic device required special attention to the diameter size of the endoprosthesis such that it was large enough to allow for full expansion of the stent which was placed within it. Undersizing of the intraluminal graft would result in failure of the prosthesis to come into sufficient contact with the inside wall of the lumen to anchor the graft in place. The present invention allows the stent to be attached within the device such that expansion of the stent simultaneously controls the expansion of the graft, without the concerns addressed above.

The radially self-expanding intraluminal device of the present invention can be deployed into a body passageway or lumen by conventional means. More specifically, the device may be inserted intraluminally by means of a catheter having a guide wire and an introducer sheath. The tubular braid is placed within the introducer sheath in a radially collapsed state. Once the sheath and tubular braid are properly positioned within the lumen, the introducer sheath is removed, and the tubular braid radially self-expands to come into intimate contact with the inner surface of the lumen. As previously described, the tubular braid is flexible and easily manipulated into proper position. Also, the intraluminal device of the present invention has an infinitely variable and adjustable diameter in the ranges between the minimum and maximum diameter of the device. Thus, the inner diameter of the lumen in which the device is inserted need not be exactly known or predetermined. The radial expansion of the braided intraluminal device will expand and conform to the shape and contours of the lumen in which it is inserted without substantial wrinkles or creases typically formed by fixed diameter intraluminal devices. The braided tube is designed to radially self-expand with a force sufficient enough to anchor the device within the lumen, without placing disruptive force on the walls of the lumen.

Figure 4:
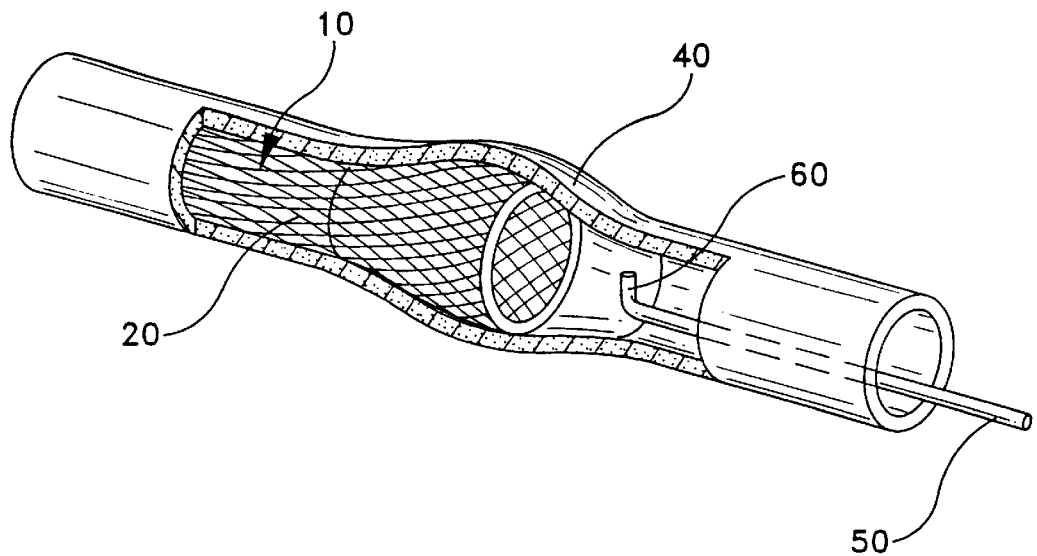
FIG. 4 is a side perspective partial cutaway view of an implanted intraluminal device of the present invention and a guidewire for repositioning the intraluminal device.

The intraluminal device of the present invention also has the advantage of being repositionable within the lumen in which it is placed even after being permitted to radially self-expand. The prior art intraluminal prosthetic devices can not be repositioned once expanded without the use of surgery because these devices are not radially collapsible after being expanded. An intraluminal prothesis may be misdeployed due to catheter malfunction or other difficulties encountered during this type of procedure. Since the intraluminal device of the present invention is in the form of a tubular braid having a diameter which decreases when longitudinally elongated, the device may be repositioned by using a guide wire having grasping means such as a finger-like member at its distal end. FIG. 4 is a side perspective partial cutaway view which illustrates a diseased blood vessel 40 showing an implanted intraluminal graft 10 and a guide wire 50 as previously described for repositioning the graft. The guide wire preferably has at least one finger-like member 60 at its distal end perpendicular to the longitudinal axis of the guidewire. The finger is used to grasp the end of graft 10 closest to the direction in which the graft is to be moved. For example, in FIG. 4, if the graft 10 is to be repositioned to the right of its present location, the finger will be used to grasp the end of the graft closest to the guide wire 50 as shown in FIG. 4. When the graft 10 is pulled by the guide wire 50, the braid yarns 20 will scissor and longitudinally expand (radially collapse), making it relatively easy to reposition the graft within the vessel.

Figure 3:
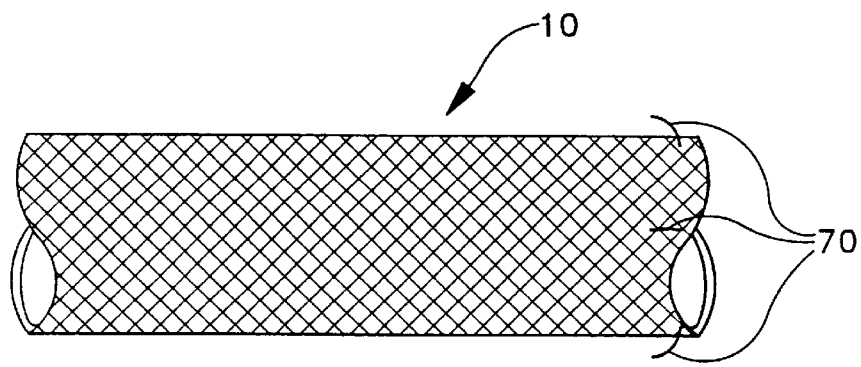
FIG. 3 is a side elevational view of an embodiment of the present invention showing anchors positioned at one end of the intraluminal device.

In an alternative embodiment, the intraluminal device may include a means for anchoring the device within the lumen in which it is inserted. An example of this embodiment is illustrated in FIG. 3. The tubular braid 10 has hooks 70 integrally formed in at least one end of the braid. Upon radial expansion, the hooks 70 slightly impinge the inner surface of the lumen or blood vessel to anchor the intraluminal device in position. In a blood vessel, the hooks 70 might only be necessary at one end of the device since the flow of blood will further serve to keep the graft in the expanded state, thereby providing sufficient contact with the lumen wall to stabilize against unwanted movement. In other body passageways, it may be advantageous to have hooks 70 at both ends to securely anchor the device in position.

In yet another embodiment, the intraluminal device of the present invention may also be formed on a shaped mandrel in order to form a braid more closely resembling the length of lumen in which it is to be inserted. Additionally, in a braided structure, it is possible to form bifurcations, trifurcations or multiple tubular structures. This may be accomplished in a continuous process as the braided device is being formed, or by joining at least two braided tubes previously formed by sewing or other appropriate means for connecting the braided structures together to form a desired formation. Thus, a braided structure is more versatile in design than conventional stents and grafts.

Thus, while these have been disclosed what are presently believed to be the preferred embodiments of the present invention, other and further manifestations of the invention will become apparent to those skilled in the art. It is intended to claim all such changes and modifications which come within the true scope and spirit of the present invention.

What is claimed is:

1. An implantable intraluminal device comprising a radially self-expanding hollow tubular braid wherein the device is made from a thermoplastic material which is heat-set for a sufficient time and temperature to effectuate a permanent memory in an expanded state and wherein the braid is a three-dimensional braid, wherein the braid further includes a stiffening component to add a greater degree of rigidity to the structure.

2. A device as described in claim 1, wherein said stiffening component comprises a metallic wire braided into said three-dimensional braid.

3. A device as described in claim 1, wherein the device is an endovascular prosthesis.

4. A device as described in claim 1, wherein the device expands under conditions found within a lumen.

5. A device as described in claim 1, wherein the device substantially conforms to the shape and inner surface of a lumen.

6. A device as described in claim 1, wherein the device is radially adjustable.

7. A device as described in claim 1, wherein the thermoplastic material is selected from the group consisting of polyester, polypropylene, polyethylene, polyurethane, and polytetrafluoroethylene.

8. A device as described in claim 1, wherein the thermoplastic material is heat conditioned at 350° F. for a time sufficient to set it in a radially expanded position.

9. A device as described in claim 1, wherein the device is in a radially expanded position under unstressed conditions.

10. A device as described in claim 1, wherein the device has a diameter in the range of about 4 mm to about 38 mm in the radially expanded position.

11. A device as described in claim 1, wherein the device has a diameter in the range of about 12 mm to about 24 mm in a longitudinally expanded position.

12. A device as described in claim 1, wherein the braid has a braid angle from about 10° to about 85°.

13. A device as described in claim 12, wherein the braid has a braid angle from about 15° to about 70°.

14. A device as described in claim 1, wherein the braid is formed from a yarn having a denier in the range of 20 to 500 denier.

15. An implantable intraluminal device, comprising a radially self-expanding hollow tubular braid, wherein the device is made from a thermoplastic material which is heat-set for a sufficient time and temperature to effectuate a permanent memory in an expanded state and wherein the braid is a three-dimensional braid, wherein the braid further includes axial yarns braided into said braid to control the amount of expansion of the device in an unstressed state.

* * * * *